(12) United States Patent
Al Taweel et al.

(10) Patent No.: US 9,872,749 B2
(45) Date of Patent: Jan. 23, 2018

(54) BITE REGISTRATION BLOCK AND BITE REGISTRATION KIT INCLUDING THE SAME

(71) Applicant: KING SAUD UNIVERSITY, Riyadh (SA)

(72) Inventors: Sara Mohammad Al Taweel, Riyadh (SA); Hanan Nejer Sahil Alotaibi, Riyadh (SA); Huda Ahmed Hanash Alshehri, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 15 days.

(21) Appl. No.: 15/169,708

(22) Filed: May 31, 2016

(65) Prior Publication Data

US 2017/0340422 A1    Nov. 30, 2017

(51) Int. Cl.
*A61C 9/00* (2006.01)
*A61C 19/05* (2006.01)
*A61C 13/00* (2006.01)
*A61C 13/267* (2006.01)

(52) U.S. Cl.
CPC .......... *A61C 19/05* (2013.01); *A61C 13/0003* (2013.01); *A61C 13/267* (2013.01)

(58) Field of Classification Search
CPC .... A61C 19/05; A61C 13/0003; A61C 13/267
USPC .......................................................... 433/71
See application file for complete search history.

(56) References Cited

U.S. PATENT DOCUMENTS

| 4,227,877 A | 10/1980 | Tureaud et al. |
| 4,657,509 A * | 4/1987 | Morris ................. A61C 9/0006 433/171 |
| 5,090,047 A | 2/1992 | Angotti et al. |
| 5,266,031 A | 11/1993 | Marigza |
| 5,299,936 A * | 4/1994 | Ueno ....................... A61C 7/08 128/861 |
| 5,580,244 A | 12/1996 | White |
| 6,196,840 B1 | 3/2001 | Zentz et al. |
| 2005/0100855 A1 | 5/2005 | Gittleman |
| 2014/0287379 A1* | 9/2014 | Chun ................... A61C 9/0006 433/42 |
| 2015/0150657 A1 | 6/2015 | Suga et al. |

FOREIGN PATENT DOCUMENTS

EP           1 844 729 A2    10/2007

* cited by examiner

*Primary Examiner* — Cris L Rodriguez
*Assistant Examiner* — Mirayda A Aponte
(74) *Attorney, Agent, or Firm* — Richard C. Litman

(57) ABSTRACT

The bite registration block is used for recording the relation between a patient's maxillary and mandibular arches for proper fabrication of a fixed dental prosthesis, or prostheses, such as fixed crowns or the like. The bite registration block is particularly adapted for use when a patient's prepared teeth are opposed by an edentulous arch (i.e., opposed by an area of missing teeth). The bite registration block is formed from a resilient material, such as a suitable type of plastic or the like, and is formed as a block having opposed upper and lower surfaces, a pair of laterally opposed side surfaces, and a pair of longitudinally opposed side surfaces. The upper surface defines a concave, longitudinally extending recess for positioning about an edentulous region of the patient's jaw.

4 Claims, 5 Drawing Sheets

BITE REGISTRATION BLOCK AND BITE REGISTRATION KIT INCLUDING THE SAME

BACKGROUND OF THE INVENTION

1. Field of the Invention

The present invention relates to the fabrication of fixed dental prostheses, such as fixed crowns, and particularly to a bite registration block used for recording the relation between a patient's maxillary and mandibular arches for proper fabrication of the fixed dental prosthesis or prostheses.

2. Description of the Related Art

In order to replace missing teeth with dental crowns, dental implants or the like, a dentist must make very precise measurements in order to properly fabricate the dental prosthesis. One of the fundamental measurements in such a process is the recording of the relationship between the upper (i.e., maxillary) and the lower (i.e., mandibular) jaws. This recordation is particularly important in the case of missing upper and lower premolars and molars (i.e., distal extension cases), where there is a lack of posterior support.

In a typical procedure, a dentist makes upper and lower negative replications (i.e., primary impressions), and these replications are then sent to a dental laboratory for pouring into a positive replication (i.e., a cast) of the patient's teeth. However, if the patient has lost multiple teeth in the posterior area, an additional procedure is required to record the relationship between the upper and lower jaws and transfer this relation to the upper and lower casts. This additional procedure is typically performed with an acrylic base material that is fabricated on the casts, attached to a wax rim to be adjusted by the dentist. This is then followed by recording the relation between the two jaws using a silicone-based registration material. This additional recording step or procedure is not only time consuming, as it requires an additional visit to the dentist, but is also more costly. Thus, a bite registration block and bite registration kit including the same solving the aforementioned problems is desired.

SUMMARY OF THE INVENTION

The bite registration block is used for recording the relation between a patient's maxillary and mandibular arches for proper fabrication of a fixed dental prosthesis, or prostheses, such as fixed crowns or the like. The bite registration block is particularly adapted for use when a patient's prepared teeth are opposed by an edentulous arch (i.e., opposed by an area of missing teeth).

The bite registration block is formed from a resilient material, such as a suitable type of plastic or the like, and is formed as a block having opposed upper and lower surfaces, a pair of laterally opposed side surfaces, and a pair of longitudinally opposed side surfaces. The upper surface defines a concave, longitudinally extending recess for positioning about an edentulous region of the patient's jaw. The bite registration block may be provided as part of a bite registration kit, including at least one piece of bite registration material and a dental clasp for supporting the bite registration block on a tooth of the patient.

These and other features of the present invention will become readily apparent upon further review of the following specification.

BRIEF DESCRIPTION OF THE DRAWINGS

Unless otherwise indicated, similar reference characters denote corresponding features consistently throughout the attached drawings.

DETAILED DESCRIPTION OF THE PREFERRED EMBODIMENTS

Figure 1:
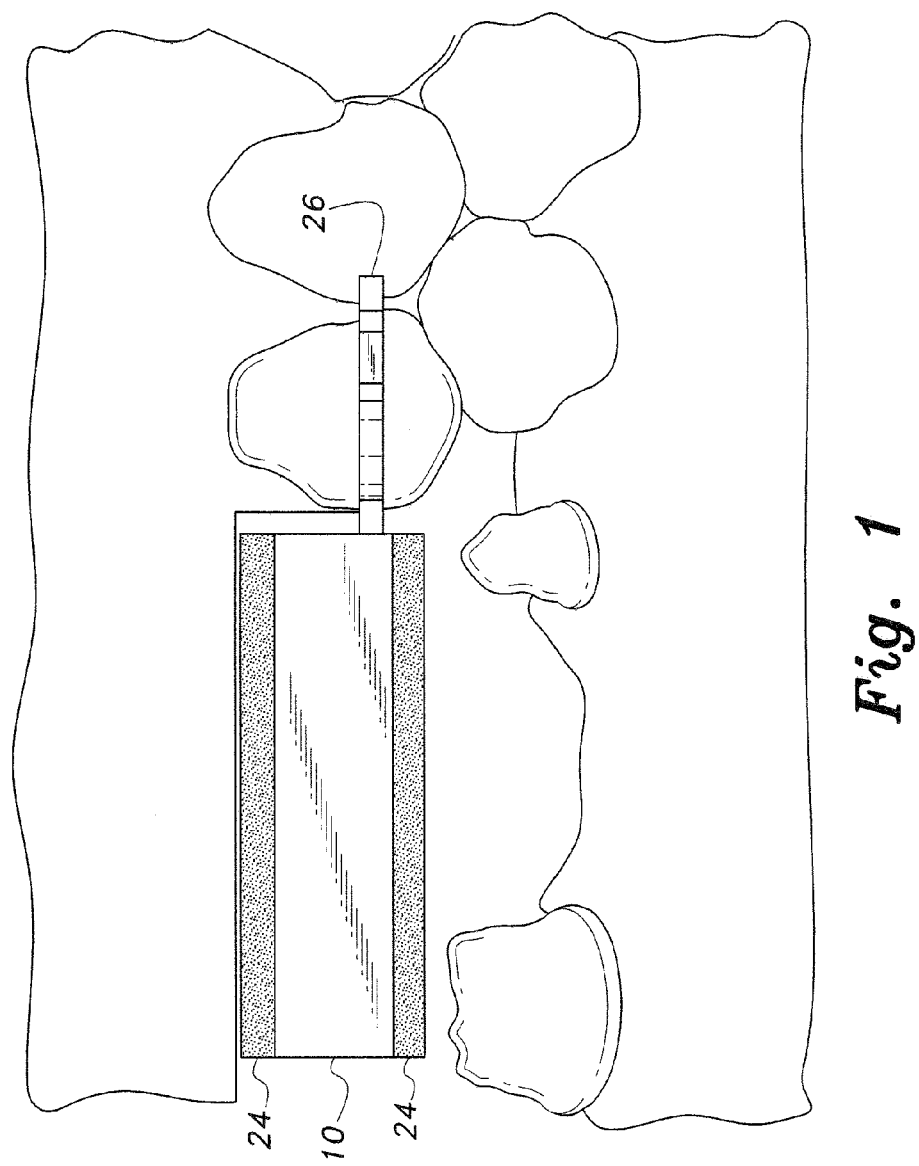
FIG. 1 is an environmental side view of a bite registration block according to the present invention.

Referring now to FIG. 1, the bite registration block 10 is used for recording the relation between a patient's maxillary and mandibular arches for proper fabrication of a fixed dental prosthesis, or prostheses, such as fixed crowns or the like. The bite registration block 10 is particularly adapted for use when a patient's prepared teeth are opposed by an edentulous arch (i.e., opposed by an area of missing teeth), as shown in the exemplary configuration of FIG. 1.

Figure 2:
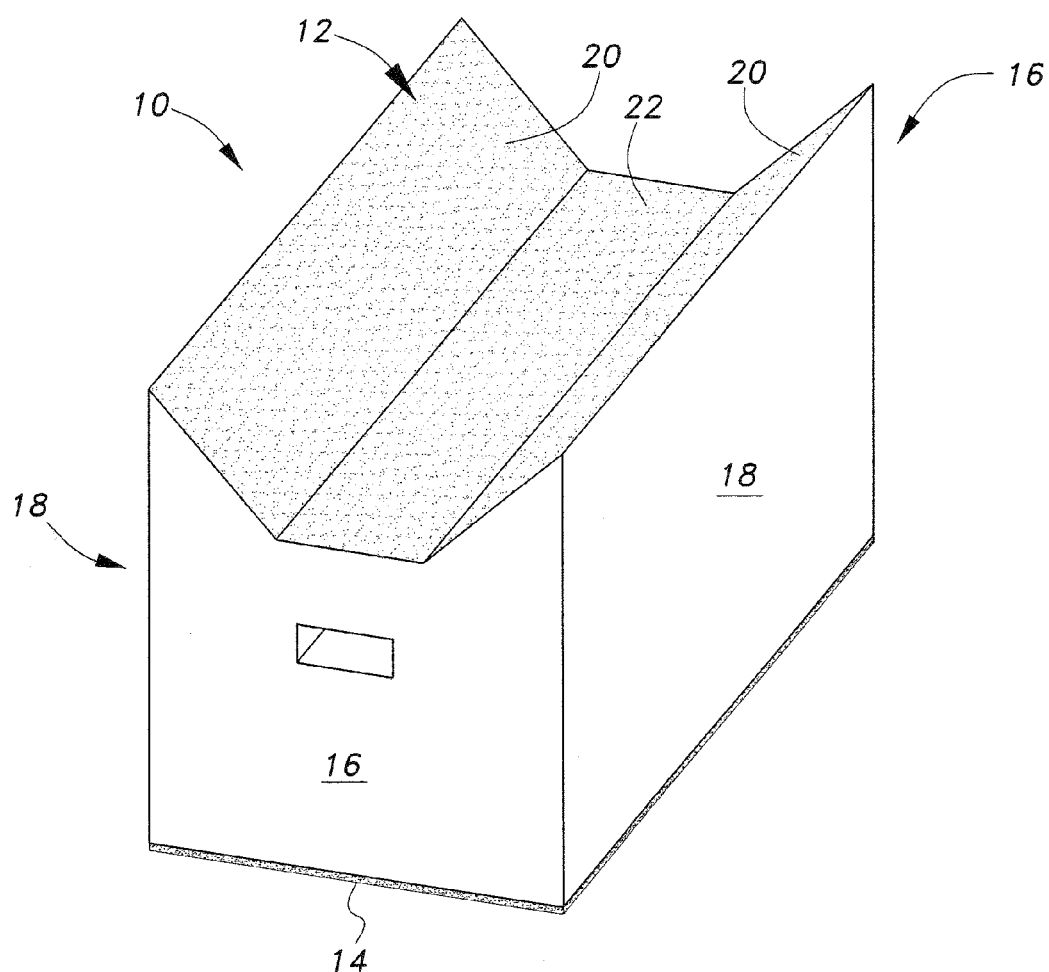
FIG. 2 is a perspective view of the bite registration block according to the present invention.

The bite registration block 10 is formed from a resilient material, such as a suitable type of plastic or the like, and, as best shown in FIG. 2, is formed as a block having opposed upper and lower surfaces, 12, 14, respectively, a pair of laterally opposed side surfaces 18, and a pair of longitudinally opposed side surfaces 16. An upper surface 12 defines a concave, longitudinally extending recess for positioning about an edentulous region of the patient's jaw, such as in the exemplary positioning shown in FIG. 1.

The upper surface 12 and the lower surface 14 are preferably each textured for frictional engagement with respective pieces of bite registration material 24, which may be any suitable type of bite registration material, as is conventionally known. As best shown in FIG. 2, the concave, longitudinally extending recess formed in upper surface 12 may be defined by a pair of opposed sloped surfaces 20 and a central surface 22 extending substantially parallel to the lower surface 14 of block 10.

Block 10 may be dimensioned as required for a particular patient and procedure. The longitudinally extending side surfaces preferably extend the length of the edentulous area received by the recess of upper surface 12 (such as in the example of FIG. 1), and the height of block 10 is preferably approximately equal to the height of the patient's posterior teeth (typically about 12 mm). The block 10 may be manufactured from plastic or the like, which can be adjusted as needed using an acrylic bur or the like, as is conventionally known.

Figure 3:
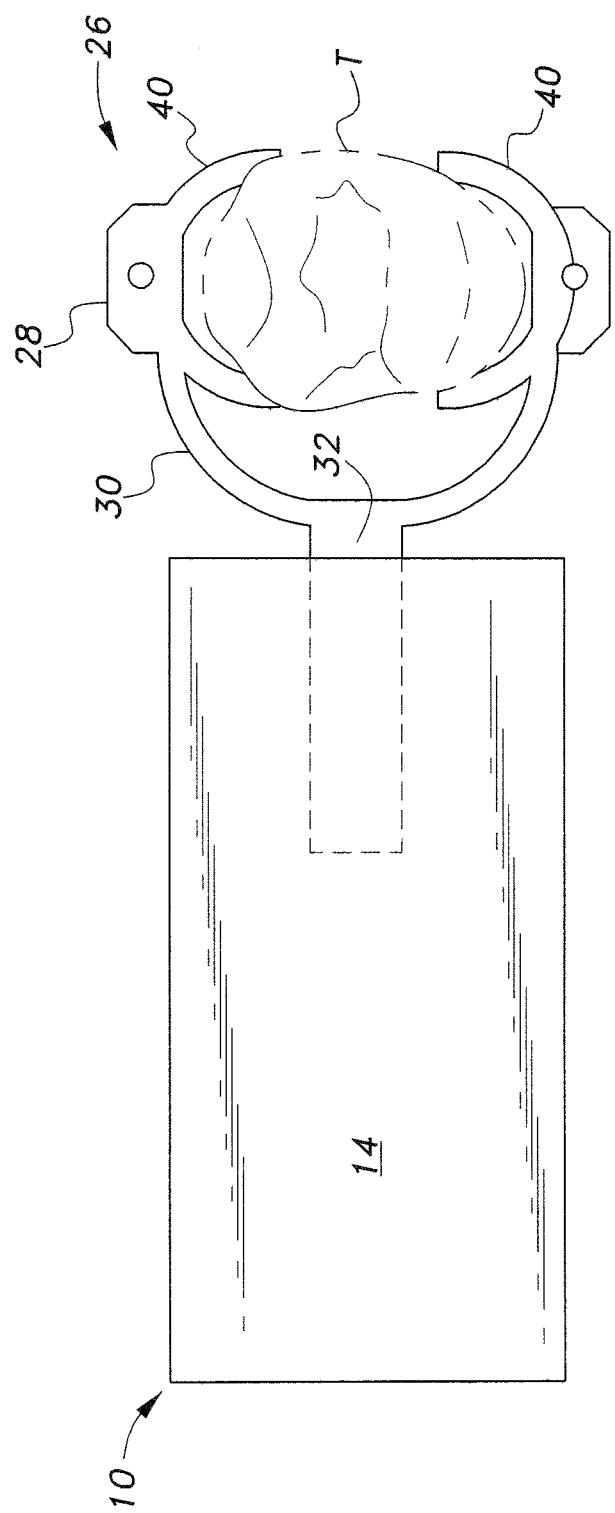
FIG. 3 is a bottom view of the bite registration block supported on a tooth by a dental clasp.
Figure 4:
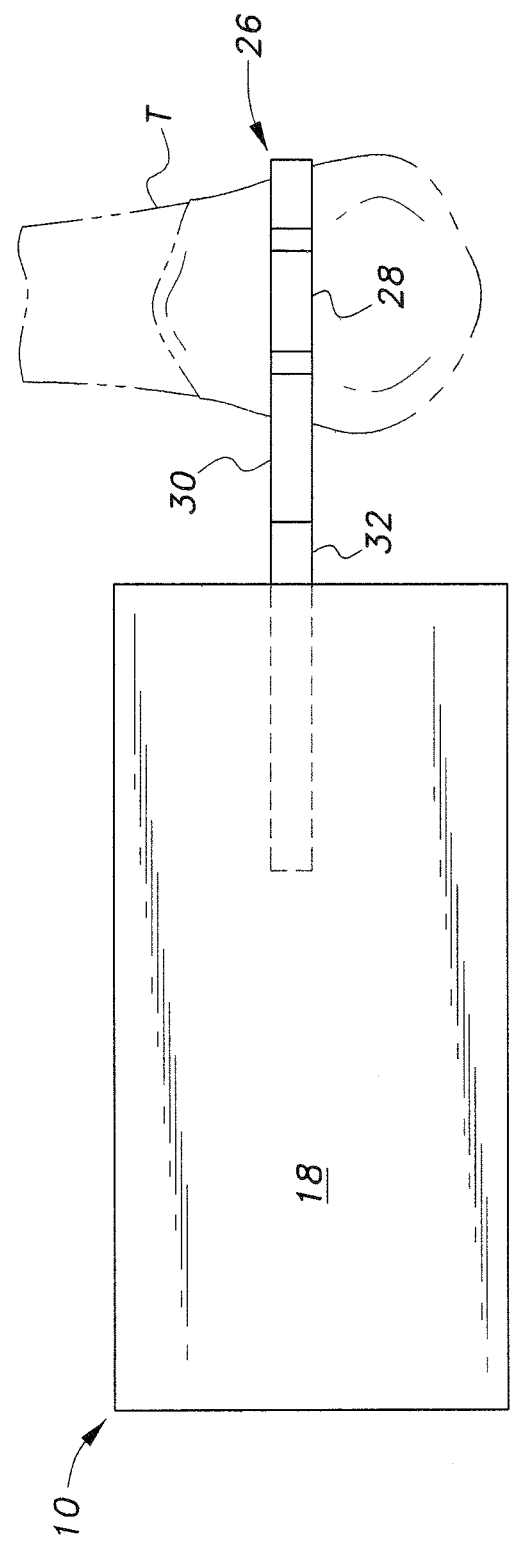
FIG. 4 is a side view of the bite registration block supported on the tooth by the dental clasp.
Figure 5:
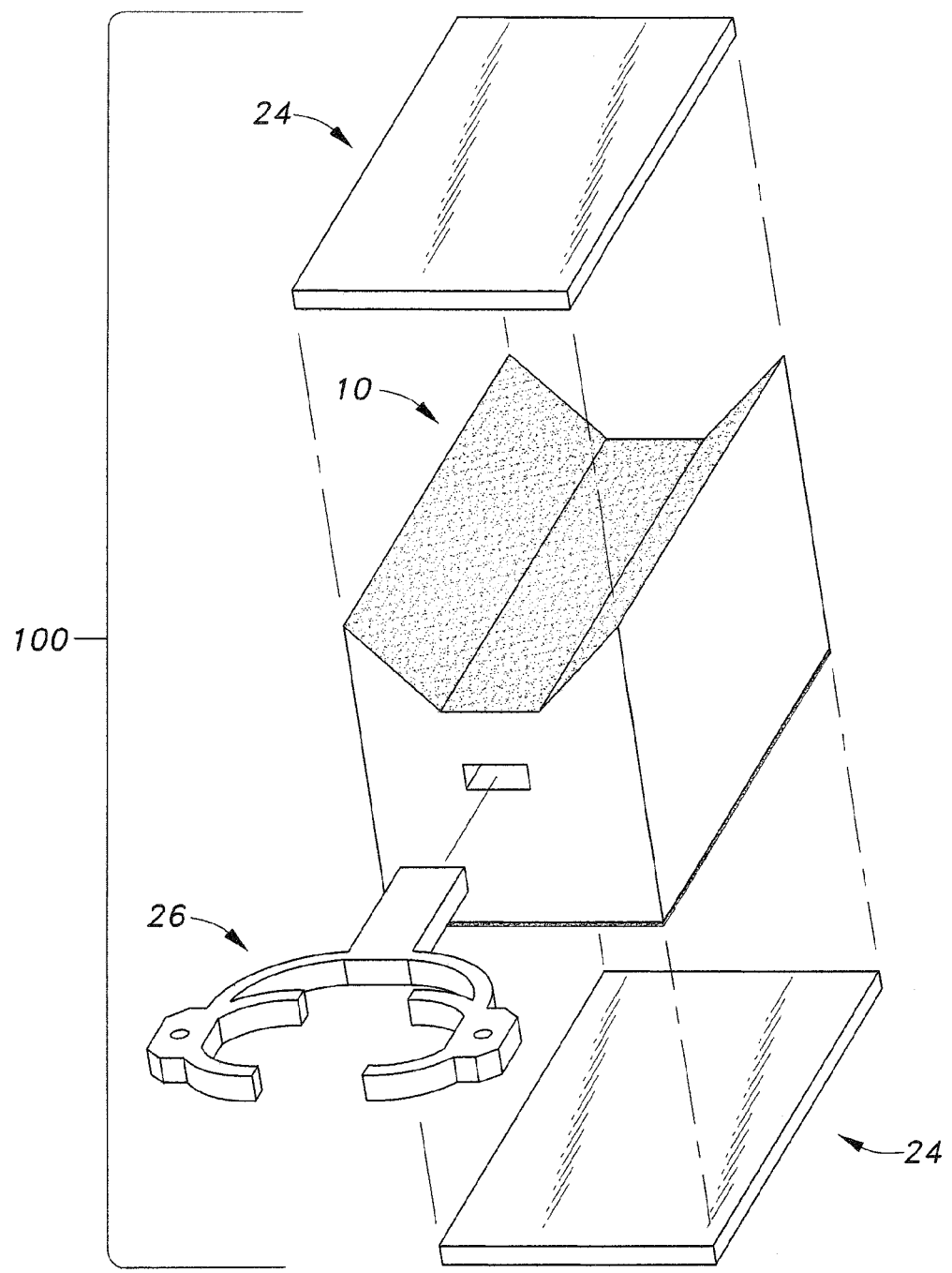
FIG. 5 is a perspective view of a bite registration kit including the bite registration block.

As shown in FIG. 5, the bite registration block 10 may be provided as part of a bite registration kit 100, including at least one piece of bite registration material 24 and at least one dental clasp 26 for supporting the bite registration block 10 on a tooth of the patient. Such dental clasps are well known in the art. As shown in FIGS. 3 and 4, a dental clasp 26, which is used to support block 10 on tooth T, includes a pair of arms 40, which are adapted for gripping the side surfaces of tooth T. Each arm 40 has an extension portion 28 having a hole formed therethrough, which are provided for engagement with a commercially available clasp holder. As is conventionally known, such a clasp holder is inserted in the holes for separation of the arms 40, allowing the arms 40 to be placed about the tooth bucco-lingually. A connector portion 30 connects the arms 40 to a joining neck 32, which is used to support the block 10.

In use, as shown in FIG. 1, the dental clasp 26 can be attached to tooth T such that the block 10 rests on the edentulous ridge of the upper arch. A piece of bite registration material 24 is placed between upper surface 12 of block 10 and the edentulous ridge to increase the adaptation between both. The lower surface 14 faces the prepared teeth on the opposing arch (i.e., the lower arch), and another piece of bite registration material 24 may be positioned on lower surface 14 for registration of the prepared teeth on the lower arch.

It is to be understood that the present invention is not limited to the embodiments described above, but encompasses any and all embodiments within the scope of the following claims.

We claim:

1. A bite registration block, comprising:
a block, the block consisting of opposed upper and lower surfaces, a pair of laterally opposed smooth continuous, uninterrupted side surfaces, and a pair of longitudinally opposed side surfaces, wherein only the upper surface defines a longitudinally extending recess for positioning about an edentulous region of a patient's jaw, the longitudinally extending recess extending continuously along the upper surface from one longitudinally opposed side surface to the other and being defined by a pair of opposed, sloped flat surfaces terminating at a central, laterally extending planar surface extending parallel to the lower surface of the block, and at least one of the upper and lower surface is textured for frictionally engaging a respective piece of bite registration material, wherein at least one of the longitudinally opposed side surfaces includes a recess and further comprising a dental clasp, the dental clasp having an end portion engaging the recess thereby being attached to the block.

2. A bite registration kit, comprising:
at least one piece of bite registration material; and
a bite registration block, the bite registration block comprising a block formed from resilient material, the block consisting of opposed upper and lower surfaces, a pair of laterally opposed continuous, uninterrupted side surfaces, and a pair of longitudinally opposed side surfaces, wherein only the upper surface defines a longitudinally extending recess for positioning about an edentulous region of a patient's jaw, the longitudinally extending recess extending continuously along the upper surface from one longitudinally opposed side surface to the other and being defined by a pair of opposed, sloped flat surfaces terminating at a central, laterally extending planar surface extending parallel to the lower surface of the block, wherein at least one of the longitudinally opposed side surfaces includes a recess and further comprising a dental clasp, the dental clasp having an end portion engaging the recess thereby being attached to the block.

3. The bite registration kit as recited in claim 2, wherein the at least one piece of bite registration material comprises a pair of pieces of bite registration material.

4. The bite registration kit as recited in claim 3, wherein each of the upper and lower surfaces is textured for frictionally engaging a respective one of the pieces of bite registration material.

* * * * *